United States Patent
Hassler et al.

(10) Patent No.: US 9,255,882 B2
(45) Date of Patent: Feb. 9, 2016

(54) OPTICAL IMAGING SYSTEM

(75) Inventors: Kai Hassler, Lucerne (CH); Martina Bucher, Zurich (CH)

(73) Assignee: Scanco Holding AG, Bruttisellen (CH)

( * ) Notice: Subject to any disclaimer, the term of this patent is extended or adjusted under 35 U.S.C. 154(b) by 184 days.

(21) Appl. No.: 14/122,832

(22) PCT Filed: Jun. 1, 2011

(86) PCT No.: PCT/CH2011/000129
§ 371 (c)(1),
(2), (4) Date: Jan. 8, 2014

(87) PCT Pub. No.: WO2011/094885
PCT Pub. Date: Aug. 1, 2011

(65) Prior Publication Data
US 2014/0151576 A1    Jun. 5, 2014

(51) Int. Cl.
*G01N 21/64* (2006.01)
*G01N 21/47* (2006.01)

(52) U.S. Cl.
CPC ............ *G01N 21/64* (2013.01); *G01N 21/4795* (2013.01); *G01N 21/6456* (2013.01); *G01N 2201/0644* (2013.01)

(58) Field of Classification Search
CPC ... G01N 21/64; G01N 21/62; G01N 21/6456; G01N 21/00
USPC ......... 250/458.1, 459.1, 461.1, 338.1, 339.11
See application file for complete search history.

(56) References Cited

U.S. PATENT DOCUMENTS

| | | | | |
|---|---|---|---|---|
| 4,758,733 A | * | 7/1988 | Mochizuki | G08B 17/107 250/574 |
| 4,851,819 A | * | 7/1989 | Kawai | G08B 17/107 250/574 |
| 4,897,634 A | * | 1/1990 | Sawa | G08B 17/107 174/377 |
| 5,430,307 A | * | 7/1995 | Nagashima | G08B 17/107 250/574 |
| 5,642,099 A | * | 6/1997 | Nagashima | G08B 17/107 250/574 |

(Continued)

FOREIGN PATENT DOCUMENTS

EP    2 166 250 A1    3/2010

OTHER PUBLICATIONS

International search report for PCT/CH2011/000129 dated Feb. 15, 2012.

*Primary Examiner* — David Porta
*Assistant Examiner* — Djura Malevic
(74) *Attorney, Agent, or Firm* — McCormick, Paulding & Huber LLP

(57) ABSTRACT

The invention relates to an optical imaging system (20) comprising an illumination unit (23), a detection unit (24) and a measurement chamber (21) for receiving a subject to be examined, wherein the illumination unit (23) is arranged such in relation to the measurement chamber (21) that it can illuminate a subject placed inside the measurement chamber (21), and wherein the measurement chamber (21) is provided with several fins (31, 31') for preventing stray light from reaching the detection unit (24), the several fins (31, 31') being arranged in such a way that at least some of the fins (31, 31') are in the field of view of the detection unit (24) with the fins (31, 31') being orientated such that the surfaces (31.1, 31.1') of the fins that are subjected to illumination by stray light are not visible to the detection unit (24).

20 Claims, 4 Drawing Sheets

(56) References Cited

U.S. PATENT DOCUMENTS

| | | | | |
|---|---|---|---|---|
| 6,195,014 B1 * | 2/2001 | Sakurai | ............... | G08B 17/107 250/574 |
| 6,756,905 B2 * | 6/2004 | Rattman | .............. | G08B 29/183 250/574 |
| 6,778,091 B2 * | 8/2004 | Qualey, III | ........... | G08B 17/107 250/574 |
| 7,697,140 B2 * | 4/2010 | Iguchi | ................. | G08B 17/107 250/574 |
| 2002/0154018 A1 * | 10/2002 | Nishikawa | ........... | G08B 17/107 340/630 |
| 2004/0238741 A1 * | 12/2004 | Gat | ........................... | G01J 5/06 250/338.1 |
| 2006/0017580 A1 * | 1/2006 | Hess | ................... | G08B 17/107 340/630 |
| 2007/0274580 A1 | 11/2007 | Ntziachristos et al. | | |
| 2009/0021729 A1 * | 1/2009 | Iguchi | ................. | G08B 17/107 356/246 |

* cited by examiner

OPTICAL IMAGING SYSTEM

CROSS REFERENCE TO RELATED APPLICATIONS

This application claims the priority of PCT Application No. PCT/CH2011/000129, filed on Jun. 1, 2011, the disclosure of which is incorporated herein by reference in its entirety.

TECHNICAL FIELD

The invention relates to an optical imaging system according to the preamble of claim 1. Such an optical imaging system can for example form part of and/or be used as a system for diffuse optical tomography (DOT), a system for fluorescence tomography (FT) or a fluorescence imaging (FI) system (for example a small animal FI system). An optical imaging system may also be referred to as scanner.

BACKGROUND OF THE INVENTION

Fluorescence tomography (FT) and diffuse optical tomography (DOT) are imaging techniques by which tomographic representations of optical properties of a subject, i.e. of its biological tissue, can be obtained in vivo. These techniques are mostly, but not exclusively, applied for preclinical small animal imaging. They may also be applied for clinical imaging including screening for breast cancer and functional imaging of the brain.

In the case of diffuse optical tomography (DOT) the obtained optical properties are usually the absorption and scattering coefficients or similar of the biological tissue of the examined subject, the coefficients relating to morphological and functional properties of the biological tissue such as vascularisation and perfusion.

In the case of fluorescence tomography (FT) a three-dimensional map of fluorescence emission is obtained by reconstruction. The map may for instance represent the distribution of fluorescent molecular markers that have been administered to the examined subject. The marker molecules bind to or are activated by their target molecules in the examined biological tissue. The measured distribution of the activated molecular markers thus represents the concentration of specific target molecules. Application of fluorescence tomography is widespread in oncology, where fluorescence tomography can for instance be used to monitor the expression level of oncogenes in cancerous tissue in mice used as mammalian animal models during research and investigation of human cancer. Fluorescence tomography (FT) is also known as fluorescence enhanced diffuse optical tomography (fDOT) or as fluorescence molecular tomography (FMT).

In diffuse optical tomography (DOT), fluorescence tomography (FT) and in fluorescence imaging (FI) (e.g. small animal FI) measurements are obtained by illuminating a part of the surface of the examined subject with a light beam and by detecting and quantifying light re-emitted from a part of the surface of the subject. Reconstruction algorithms are used to reconstruct an image or images of the subject from the measured data. Minor variations exist in the way illumination and detection are performed and in the reconstruction algorithms employed.

The illumination of the subject is typically, but not necessarily, point-like and is achieved with monochromatic light that preferably has a wavelength in the near-infrared (NIR) spectrum. The detection and measurement of the light that is (re-)emitted from the subject is realized by imaging the re-emitting part of the examined subject onto a detection unit with an electro-optical sensor such as a CCD (charge-coupled device) sensor or a CMOS (complementary metal oxide semiconductor) sensor. This imaging may be repeated for different illuminated points on the subject.

In the case of diffuse optical tomography (DOT) the light that impinges onto the biological tissue propagates within/ through the biological tissue of the subject and emerges from a part of the surface of the biological tissue, with the emerging light being measured. Fluorescence tomography (FT) often also comprises measurement of the illuminating/excitation light in addition to the measurement of the fluorescence (signal) intensity that arises at the surface of the examined subject. Measurement of the fluorescence intensity is typically realized by using appropriate filters in the detection path that efficiently block the wavelength of the illumination/excitation light but that are transparent at least for a part of the emitted fluorescence spectrum.

Biological tissue has, however, the property of strongly scattering visible and near-infrared (NIR) light. Hence, each photon that penetrates the biological tissue and propagates through it undergoes a large amount of scattering events before it is either absorbed by the biological tissue or re-emitted from it. The light propagation through and within the biological tissue is often modelled as diffusion process with the corresponding diffusion equation, although other models are sometimes used. Accordingly, the reconstruction algorithms used in diffuse optical tomography (DOT) and fluorescence tomography (FT) are usually based on the diffusion equation. The diffusion equation can be solved within an FEM (finite element method) or a FVM (finite volume method) framework with boundary data being given by the measured surface images of the examined subject, the solution of the diffusion equation yielding the distribution of the scattering and absorption coefficients or the fluorophore concentration.

A common arrangement of the illumination unit and the detection unit in an optical imaging system such as for DOT, FT or FI is such that illumination and detection are realized on opposite sides of the examined subject. An optical imaging system realized in such a way is also called transillumination system as the light transmitted through the subject is detected. FIG. 1 schematically depicts a possible implementation of such a transillumination DOT or FT system/optical imaging system 1. The illumination unit is realized by a laser 2 as light source that is pointed at the examined subject 3 such that its beam impinges onto the surface of the examined subject 3. FIG. 1 shows a mouse as exemplary subject. The optical imaging system 1 is, however, not limited to imaging mice or even biological specimen. The detection unit comprises a camera 4, a lens (not shown) and a rotatable set of filters 5 (also referred to as filter changer). The lens is arranged between the camera 4 and the set of filter 5. The set of filters 5 can be rotated such that different filters can be positioned in front of the lens depending on the particular application. The illumination unit 2 and the detection unit 4, 5 are mounted opposite each other on a rotatable platform/gantry 6, wherein the platform 6 has a central opening 7 with a dedicated holder 8 for receiving the subject 3 to be examined. The illumination unit 2 and the detection unit 4, 5 are arranged on opposite sides of the subject 3/the central opening 7. The platform 6 can be rotated as indicated by the arrow 9 such that transillumination of the subject 3 (and thus illumination and detection) can be performed at various angles with respect to the subject 3. Accordingly, an optical imaging system as depicted in FIG. 1 is also referred to as system for 360°-projection free-space fluorescence tomography. The holder 8 onto which the subject 3 is placed can be moved/shifted along the rotation axis 10 (translatory movement) of the platform 6 such that transillumination (and thus illumination and detection) can be performed at various positions of the subject 3 along the rotation axis 10.

Variations of the optical imaging system shown in FIG. 1 are described in the literature, including systems where the examined subject can be rotated and/or the illumination unit and the detection unit can be translatorily moved. Furthermore, optical imaging systems are known that provide further degrees of freedom for scanning the laser beam/the light (re-)emerging from the subject.

In an optical imaging system for transillumination (as depicted in FIG. 1), e.g. in systems for FT, DOT or FI (for example small animal FI) that use transillumination, light has to traverse a relatively large volume of biological tissue before a signal is emitted from the subject for detection by the detection unit at the side of the subject that is opposite to the entry point of the light beam/illuminating light. As mentioned above, biological tissue strongly scatters, reflects and absorbs light. Thus light propagation in biological tissue typically has a diffusive nature and most of the injected photons of the illuminating light become absorbed or diffusively reflected by the biological tissue, resulting in a very low measured signal (which is typically radiant power or radiant flux). The power of the part of the illuminating light that is diffusely reflected at the illuminated surface area of the subject (the reflected light) is typically of orders of magnitude higher than that of the signal to be measured. Furthermore, this reflected light (also called stray light or spurious stray light) can reach the detection unit via secondary reflections. The power of this spurious stray light can easily be high enough to saturate the detection unit or simply to lead to false measurement results. However, in particular in so called 360°-projection free-space fluorescence tomography systems as exemplarily depicted in FIG. 1 it is difficult to protect the detection unit from such stray light (also called background signals or background noise). To shield the subject to be examined from ambient light, the subject is enclosed in a light-tight, opaque chamber, whereby ambient light is to be distinguished from stray light.

In conventional FT, DOT or FI systems (e.g. small animal FI systems) planar optical imaging systems are used that do not allow for rotation of the illuminating unit and the detection unit around the subject. In these conventional planar optical imaging systems transillumination is performed from below the subject and detection takes place from above the subject. Light-shielding structures can be arranged very close to or even in contact with the subject's body. The subject, e.g. an animal, can for example be placed on a black surface that serves as shielding, the black surface having a window just below the subject's body to allow illumination to pass through the window and to impinge on the subject. Different implementations of relevant commercial planar FT and FI imaging systems are reviewed and discussed in F. Leblond et al., "Pre-clinical whole-body fluorescence imaging: Review of instruments, methods and applications", Journal of Photochemistry and Photobiology B: Biology 98 (2010), pp. 77-94.

The above-described light-shielding solution that is employed for planar optical imaging systems is, however, not appropriate for optical imaging systems that provide a scanner function, where the detection and the illumination units rotate around the subject to perform measurements at different angles (as in the 360°-projection free-space fluorescence tomography system depicted in FIG. 1). The use of light-absorbing surfaces (for example through surface blackening) may alleviate the stray light problem, but does in many cases not lead to a sufficient reduction of stray light. Optical imaging systems that allow for rotation are, however, superior to planar optical imaging systems as they allow to image the subject from different angles and to thus acquire a much higher amount of relevant measurement data leading to an improvement in the reconstruction quality.

A 360°-projection free-space fluorescence tomography system, wherein the illumination unit and the detection unit rotate relatively to a subject animal, is discussed in combination with an X-ray CT (computer tomography) scanner in R. B. Schulz et al., "Hybrid Fluorescence Tomography/X-ray Tomography improves reconstruction quality", Proceedings of SPIE-OSA Biomedical Optics, SPIE Vol. 73720 (2009), 73700H-1-73700H-4. The stray light problem is not addressed.

In practice some light-absorbing surfaces positioned behind the subject to be examined will be in the field of view of the detection unit. In existing rotating DOT and FT systems these surfaces will then be illuminated by light reflected from the surface of the examined subject, i.e. by stray light. Intensities occurring at these surfaces can easily reach intensities that are high enough to lead to a saturation of the detection unit and can thus disturb the measurements of the (re-)emitted/transmitted light or of the arising fluorescence intensities. Moreover, the light that is reflected from the examined subject (i.e. the stray light) can bias the measurement results by additionally illuminating parts of the subject through multiple reflections. Such stray light problems can limit the performance of an optical imaging system due to low signal strength of the measured/detected signal, even if the significant surfaces of the system and light shielding structures which protrude into the field of view of the detection unit are blackened to enhance their light absorbance characteristics and light filters are used.

Patent document U.S. Pat. No. 6,462,889 B1 discloses a supersonic missile that comprises an optical system. Baffles are employed to reduce the effects of stray light. The missile does not comprise an active light source/illumination source and can not be used to image/scan a subject arranged inside the missile.

SUMMARY OF THE INVENTION

It is an object of the invention to provide an optical imaging system with which the effects and contribution of spurious stray light can be reduced. It is a further object of the invention to provide an optical imaging system in which the amount of stray light that impinges on the detection unit of the optical imaging system is reduced.

In order to implement these and still further objects of the invention, which will become more readily apparent as the description proceeds, an optical imaging system is provided that comprises an illumination unit, a detection unit and a measurement chamber for receiving a subject to be examined. The illumination unit is arranged such in relation to the measurement chamber that it can illuminate a subject placed inside the measurement chamber. The detection unit is preferably arranged on that side of the measurement chamber that is opposite to the side of the measurement chamber where the illumination unit is arranged. However, the imaging unit and the detection unit can, for example, also be arranged such that the light beam of the imaging unit and the optical axis of the detection unit intersect at an angle of 45 degrees. The measurement chamber is provided with several fins for preventing stray light from reaching the detection unit, the several fins being arranged in such a way that at least some of the fins are in the field of view of the detection unit. Preferably all fins are in the field of view of the detection unit. The fins are orientated such that the surfaces of the fins that are subjected to illumination by stray light are not visible to the detection unit.

By preventing stray light from entering the detection unit more accurate measurement results can be obtained that correspond to an image of the examined subject as the signal-to-noise ratio is increased.

The optical imaging system according to the invention can, but does not have to, be employed as fluorescence tomography (FT) system, as diffuse optical tomography (DOT) system or as part of such a system, the signal(s) detected by the detection unit serving as input for a FT or a DOT reconstruction algorithm. It can also be employed as fluorescence imaging (FI) system (e.g. as small animal FI system) or as part thereof.

The optical imaging system according to the invention can be realized as planar optical imaging system/scanner or as part thereof. The optical imaging system according to the invention can, however, also be realized as rotatable optical imaging system or as part thereof, wherein the illumination unit and the detection unit are rotatable with respect to the subject and/or wherein the subject to be examined can be rotated (such as in X-ray CT-like scanning devices/systems).

To avoid or at least to reduce the effects of stray light the optical imaging system according to the invention employs structural components in form of fins that are arranged to comply with certain geometrical constraints/concepts and does not solely rely on enhancing the light absorption properties of the relevant surfaces of the system that are in the field of view of the detection unit, e.g. through blackening of these surfaces, which is often not enough to sufficiently reduce stray light. Enhancing the light absorption properties of these surfaces, in particular by blackening, can however be employed in addition to the specifically arranged fins of the optical imaging system of the invention.

BRIEF DESCRIPTION OF THE DRAWINGS

Further advantageous features and applications of the invention can be found in the dependent claims as well as in the following description of the drawings illustrating the invention. In the drawings like reference signs designate the same or similar parts throughout the several figures of which:

FIG. 1 has already been described in the introductory part of the description and reference is made thereto.

DESCRIPTION OF PREFERRED EMBODIMENTS

Figure 1:
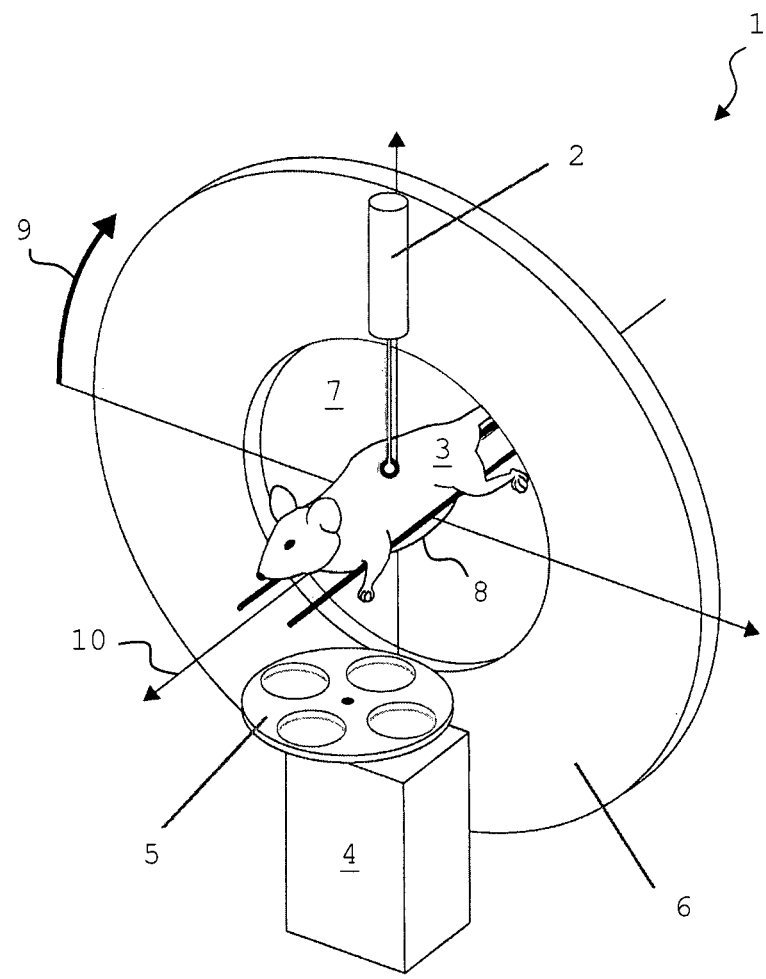
FIG. 1 depicts a known optical imaging system in the form of a 360°-projection free-space fluorescence tomography system.
Figure 2:
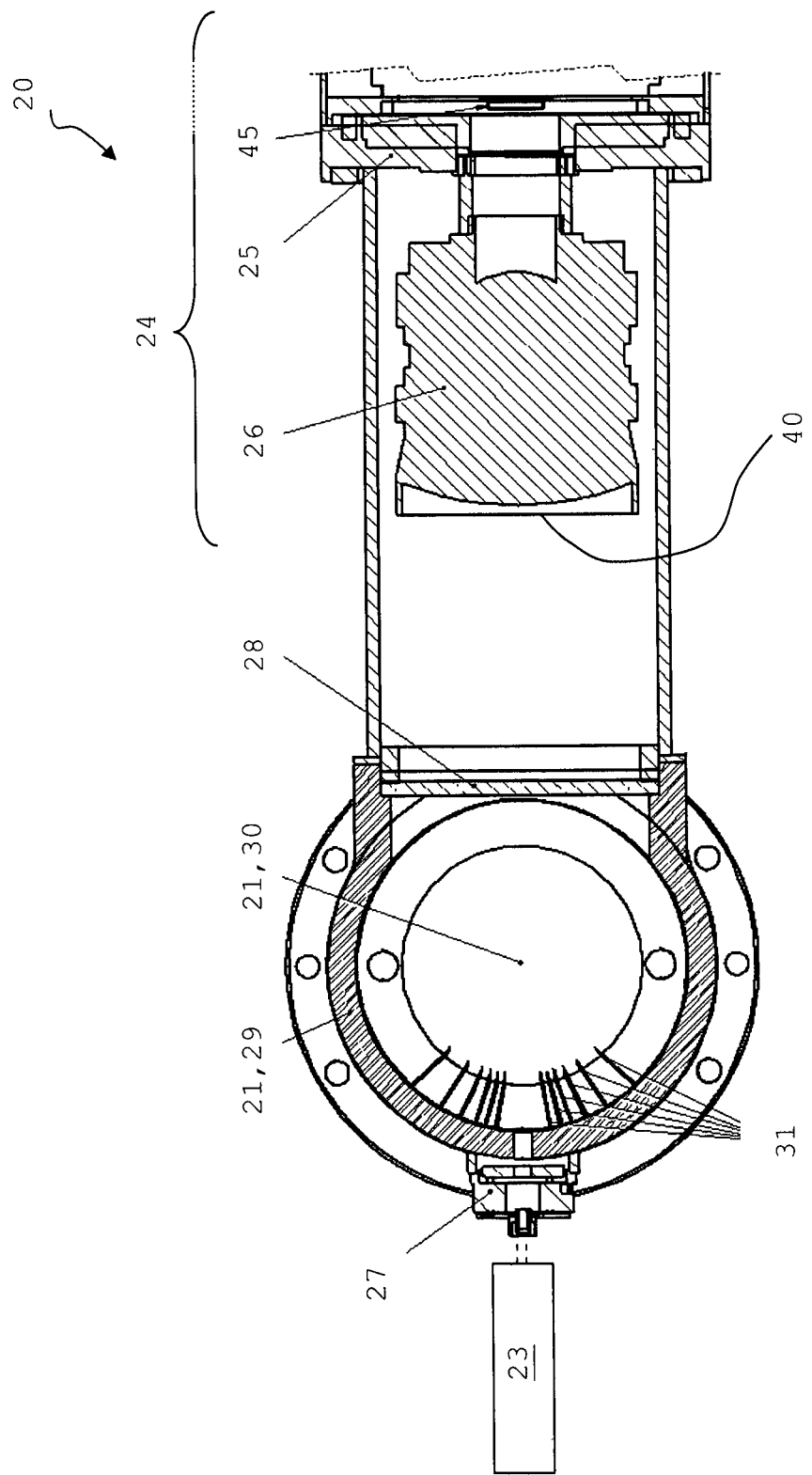
FIG. 2 depicts a cross-section of an optical imaging system according to the invention.

FIG. 2 shows an optical imaging system 20 according to the invention. The optical imaging system 20 comprises a measurement chamber 21 for receiving a subject to be examined, an illumination unit 23 and a detection unit 24 (also called detector). The illumination unit 23 in particular employs a laser as light source as shown in FIG. 1. An incandescent lamp, in particular with appropriate filters, may for example also be employed as illumination unit 23. The use of other light sources is of course possible. With the illumination unit 23 a point-like illumination can preferably be realized on the optical axis of the optical imaging system 20. The detection unit 24 preferably comprises a camera 25 (shown only partly for simplicity) and a lens 26. The measurement chamber 21 is equipped with an illumination port 27 and a detection port 28. Through the illumination port 27 the light beam of the illumination unit 23 can pass into the measurement chamber 21 to illuminate the subject. Through the detection port 28 light can pass from the measurement chamber 21 to the detection unit 24 for signal detection and measurement.

The illumination unit 23 and the detection unit 24 and accordingly the illumination port 27 and the detection port 28 are preferentially arranged on opposite sides of the measurement chamber 21. The illumination unit 23 and the detection unit 24 may be arranged—each partly or entirely—inside the measurement chamber 21 or outside of the measurement chamber 21, the latter shown in FIGS. 2 and 3. If they are arranged inside the measurement chamber 21 they are enclosed by it. The illumination unit 23 and the detection unit 24 of the optical imaging system 20 according to the invention may be, but do not have to be, arranged on a rotatable platform/gantry as shown in FIG. 1. Also, the optical imaging system 20 according to the invention may be designed to provide images taken from different views of the subject. However, it can also be designed to take images from only one view of the subject.

The measurement chamber 21 has preferably opaque walls and is in particular formed as a hollow tube 29 (for its inherent cylindrical symmetry) such that ambient light can be prevented from disturbing the measurement results and an operator can be protected from the radiation of the illumination unit which is preferably laser radiation. The inner diameter of the tube 29 may for example be 90 mm. The measurement chamber 21 may of course also have a non-cylindrical form. For examination the subject is placed on the rotation axis 30 of the tube 29 with the longitudinal axis of the subject being aligned with the rotation axis 30 of the tube 29.

At the point of intersection 36 (cf. FIG. 3) of the light beam (preferably a laser beam) of the illumination unit 23 with the surface of the subject diffuse reflection of the light occurs (in addition to transmission through the subject and absorption within the subject), resulting in an additional 'light source' being created at the point of intersection 36 that illuminates the inner wall of the tube 29/the measurement chamber 21 with stray light. This additional light source may be modelled as a point (so-called point-source model) even in case of light from the illumination unit 23 penetrating the subject and emerging from all over its surface, as the radiant exitance at the surface of the subject quickly decreases with increasing distance between the point of intersection 36 and the surface of the subject from which the light emerges.

To prevent that light that is reflected at the point of intersection 36, i.e. stray light, reaches the detection unit 24 through a (second) reflection at the inner wall of the tube 29/the measurement chamber 21, the inside of the measurement chamber 21 of the optical imaging system 20 is provided with several fins 31 that prevent the stray light from reaching the detection unit 24 and hence from disturbing the measurement results. The fins 31 are preferably arranged at the inner wall of the tube 29/the measurement chamber 21 at a distance from each other (in cross-sectional view perpendicular to the longitudinal direction/rotation axis of the tube 29/the measurement chamber 21). The distance from each other may vary between the various fins 31. The fins 31 are preferentially arranged in the field of view of the detection unit. They are preferably placed on the side of the measurement chamber 21 that is opposite the detection port 28 and the detection unit 24.

By means of the fins 31 the area of the inner wall of the tube 29/the measurement chamber 21 that is illuminated by stray light (i.e. illuminated area of the inner wall of the tube 29/measurement chamber 21) is shielded from the view of the detection unit 24. To achieve this, the fins 31 are oriented such that the surfaces 31.1 of the fins 31 that may be subject to illumination by stray light are not visible to the detection unit 24. In addition, the fins 31 are orientated such that their surfaces 31.2 that are visible to the detection unit 24 and that are opposite to the surfaces 31.1 are hence not (or only marginally) illuminated by stray light (confer FIG. 3).

Figure 3:
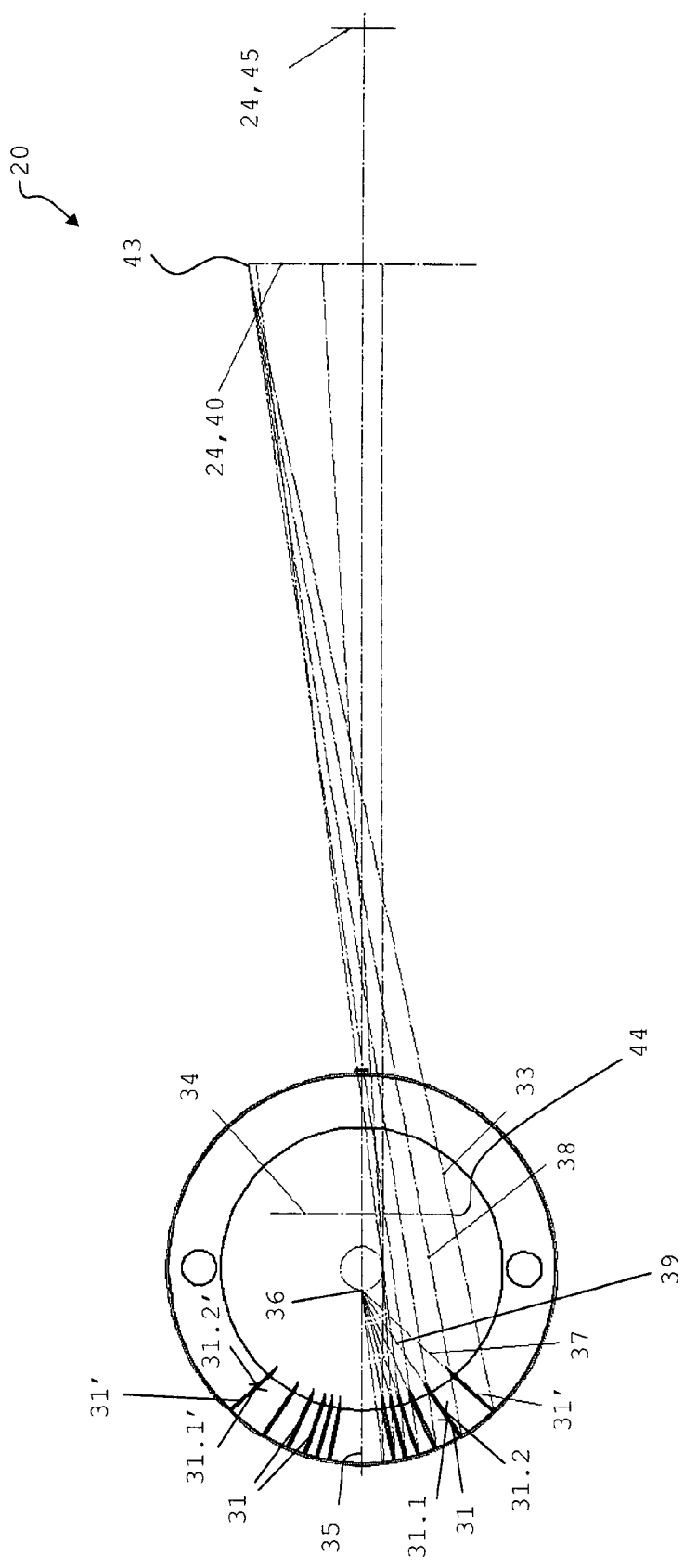
FIG. 3 depicts a cross-section of the measurement chamber, the fins and the entry of the detection unit, in particular in the form of an entrance pupil, of the optical imaging system depicted in FIG. 2 with rays of light being shown.

FIG. 3 shows a simplified version of the optical imaging system 20 depicted in FIG. 2 with light rays/light paths being depicted, wherein among others the illumination unit 23 has been omitted and only the entry 40 of the detection unit 24, which is realized as entrance pupil of the detection unit 24, is shown for reasons of simplicity. The diameter of the entrance pupil 40 is preferably 52.5 mm. The distance of the rotation axis 30 of the tube 29/the measurement chamber 21 to the entry/entrance pupil 40 is preferable about 232.1 mm.

The outermost fins 31' are preferentially, but not necessarily, mounted at the outer borders of the area of the inner wall of the tube 29 that may be illuminated by and reflect stray light and that can contribute to the impinging of stray light on the detection unit 24 (in cross-sectional view perpendicular to the rotation axis of the optical imaging system 20 (scanning system)/longitudinal direction of the tube 29 as shown in FIG. 3). The outer borders of this area are defined by the intersection of the outermost rays 33 with the inner wall of the tube 29/the measurement chamber 21 (only one outermost ray 33 is depicted in FIG. 3). The outermost rays 33 are defined as the rays that pass through an edge 43 of the entry 40 of the detection unit 24 and through an edge 44 of a projection of the light receiving region of the detection unit 24, in particular of the light receiving region of its sensor 45 (such as a CCD sensor; see FIG. 2), onto the subject plane 34 inside the measurement chamber 21, the edge 43 of the entry 40 being on the opposite side of the optical axis 35 of the optical imaging system 20. The subject plane 34 is defined as that plane inside the measurement chamber 21 that is displayed sharply in the image taken by the detection unit 24. The subject plane 34 is thus defined by the criterion that its image is in focus. The subject plane 34 is also called plane of focus or object plane in the literature relating to optics (confer also to http://en.wikipedia.org/wiki/Scheimpflug_principle, http://de.wikipedia.org/wiki/Scheimpflugsche_Regel). The distance between the rotation axis 30 of the tube 29/the measurement chamber 21 and the subject plane 24 is preferably about 12.5 mm. Rays resulting from a higher number of reflections than the second reflection are preferentially disregarded for simplicity.

The outermost fins 31' are mounted at the intersection of the outermost rays 33 with the inner wall of the tube 29/the measurement chamber 21 and project inside/into the tube 29/the measurement chamber 21. The inclination of an outermost fin 31' is given by the inclination of the ray 37 that runs from the intersection of the outermost ray 33 with the inner wall of the tube 29/the measurement chamber 21 to the point of (initial/first) intersection 36 of the light beam of the illumination unit 23 with the surface of the subject to be examined. I.e. the outermost fins 31' run along their respective rays 37. As a consequence the surface 31.2' visible to the detection unit 24 and its sensor 45, respectively, is not illuminated by stray light coming from the subject, with the area of the inner wall of the tube 29/the measurement chamber 21 that is shielded from the view of the detection unit 24 being enlarged.

The outermost fins 31' may also be arranged outside the field of view of the detection unit 24. Alternatively, they may also be arranged inside the field of view of the detection unit 24, i.e. they do not need to be arranged exactly on the edges of the field of view of the detection unit 24.

Between each outermost fin 31' and the optical axis 35 (i.e. between the two outermost fins 31') of the optimal imaging system 20 further fins 31 are arranged. These fins 31 are mounted at the inner wall of the tube 29/the measurement chamber 21 at the intersection of a ray 38 that passes preferably through an edge 43 of the entry 40 of the detection unit 24 and through the inwardly projecting end of the adjacent, more outwardly mounted fin 31, 31' on the opposite side of the optical axis 35. The expression "inwardly projecting" means projecting into the measurement chamber 21/the tube 29. The expression "outwardly mounted" relates to the distance between the respective mounting point and the optical axis 35 in the cross-sectional view depicted in FIGS. 2 and 3, with "more outwardly mounted" meaning mounted further away from the optical axis 35 at the inner wall of the tube 29/the measurement chamber 21. The fins 31 are thus placed at the outer border of that area of the inner wall of the tube 29/measurement chamber 21 that may be illuminated by stray light and that is not already shielded by more outwardly mounted fins 31, 31' from the view of the detection unit 24.

The distance between the respective mounting points of the fins 31, 31' may, however, be smaller or greater as indicated above.

As with the outermost fins 31', the inclination of a fin 31 corresponds to the inclination of the ray 39 that runs from the intersection of the ray 38 with the inner wall of the tube 29/the measurement chamber 21 to the point of (initial/first) intersection 36 of the light beam with the surface of the subject to be examined. However, a steeper inclination of the fins 31, 31' may be chosen to account for the approximate nature of the point-source model employed to model the diffuse reflections of the light beam by the surface of the subject and any inaccuracies of this model.

The provision of further fins 31 between the outermost fins 31' leads to further shielding of the area of the inner wall of the tube 29/the measurement chamber 21 that may be illuminated by stray light from the view of the detection unit 24 and that may be imaged onto the detection unit 24. As mentioned the arrangement of these additional fins 31 takes into account the area that is already shielded by more outwardly arranged fins 31 including the outermost fins 31'. The inwardly projecting ends of all the fins 31, 31' are preferably not arranged on a circle.

If, for example, six fins 31, 31' are provided, their respective inclination/angles (with respect to the optical axis 35 of the optical imaging system 20) and their extension into the tube 29/the measurement chamber 21 (i.e. their respective width) are for example as follows, starting from the outermost fin 31' to the innermost fin 31 (the fin 31 arranged closest to the optical axis 35): the first and outermost fin 31' has an inclination/angle of 47.85 degrees and a width between 14 mm and 15 mm (in particular 14.5 mm), the second fin 31 has an inclination/angle of 34.5 degrees and a width between 14 mm and 15 mm (in particular 14.5 mm), the third fin 31 has an inclination/angle of 25.58 degrees and a width between 14 mm and 15 mm (in particular 14.5 mm), the fourth fin 31 has an inclination/angle of 19.51 degrees and a width between 14 mm and 15 mm (in particular 14.5 mm), the fifth fin 31 has an inclination/angle of 15.21 degrees and a width between 14 mm and 15 mm (in particular 14.5 mm), and the sixth and innermost fin 31 has an inclination/angle of 11.12 degrees and a width between 14 mm and 15 mm (in particular 14.5 mm). The mentioned numbers for the inclinations/angles and the widths shall not be limiting in any way and are of exemplary nature. The inwardly projecting end of each fin 31, 31' may be slanted to decrease the amount of (stray) light that might be reflected by these ends.

Of course, the position and inclination of the fins 31, 31' can be determined and the fins 31, 31' can accordingly be arranged at the inner wall of the tube 29/the measurement chamber 21 by starting with the innermost fins and progressing to the outermost fins 31'.

The arrangement and the mounting points of the fins 31, 31' may be determined in a more stringent way by (preferably concurrently) considering all rays that pass through the entry 40 of the detection unit 24 and impinge on the sensor 45 of the detection unit 24 and that intersect with the area of the inner wall of the tube 29/the measurement chamber 21 that may be illuminated by stray light and reflect light onto the sensor 45 when no fins are provided. It is noted, that the mounting points of the fins 31 including the outermost fins 31' do not necessarily need to coincide with the outer borders of this area.

Regarding the point of intersection 36 of the light beam of the illumination unit 23 and the surface of the subject to be examined, for the design of the optical imaging system 20 and the design and arrangement of the fins 31, 31' a subject may be assumed whose intersected surface is located as far away as possible from the illumination unit 23 and the side of the measurement chamber 21/the tube 29, respectively, on which the illumination unit 23 is arranged. I.e. for the design of the optical imaging system 20 and the design and arrangement of the fins 31, 31' a virtual point of intersection may be chosen that is as far away as possible/as imaginable from the illumination unit 23 and the corresponding inner wall of the measurement chamber 21/the tube 29, respectively. Preferentially, this virtual point of intersection 36 is chosen such that it is situated further away from the illumination unit 23, i.e. the inner wall of the tube 29/the measurement chamber 21 where the illumination unit 23 is arranged, as any real/actual point of intersection of the light beam with the surface of a subject to be examined, with the virtual point of intersection 36 being preferably not located further away from the illumination unit 23 as necessary to fulfil the condition of being further away from this real/actual point of intersection. The distance between the rotation axis 30 of the tube 29/the measurement chamber 21 to the virtual point of intersection is preferably between 0 mm to 20 mm, in particular 5 mm.

Figure 4:
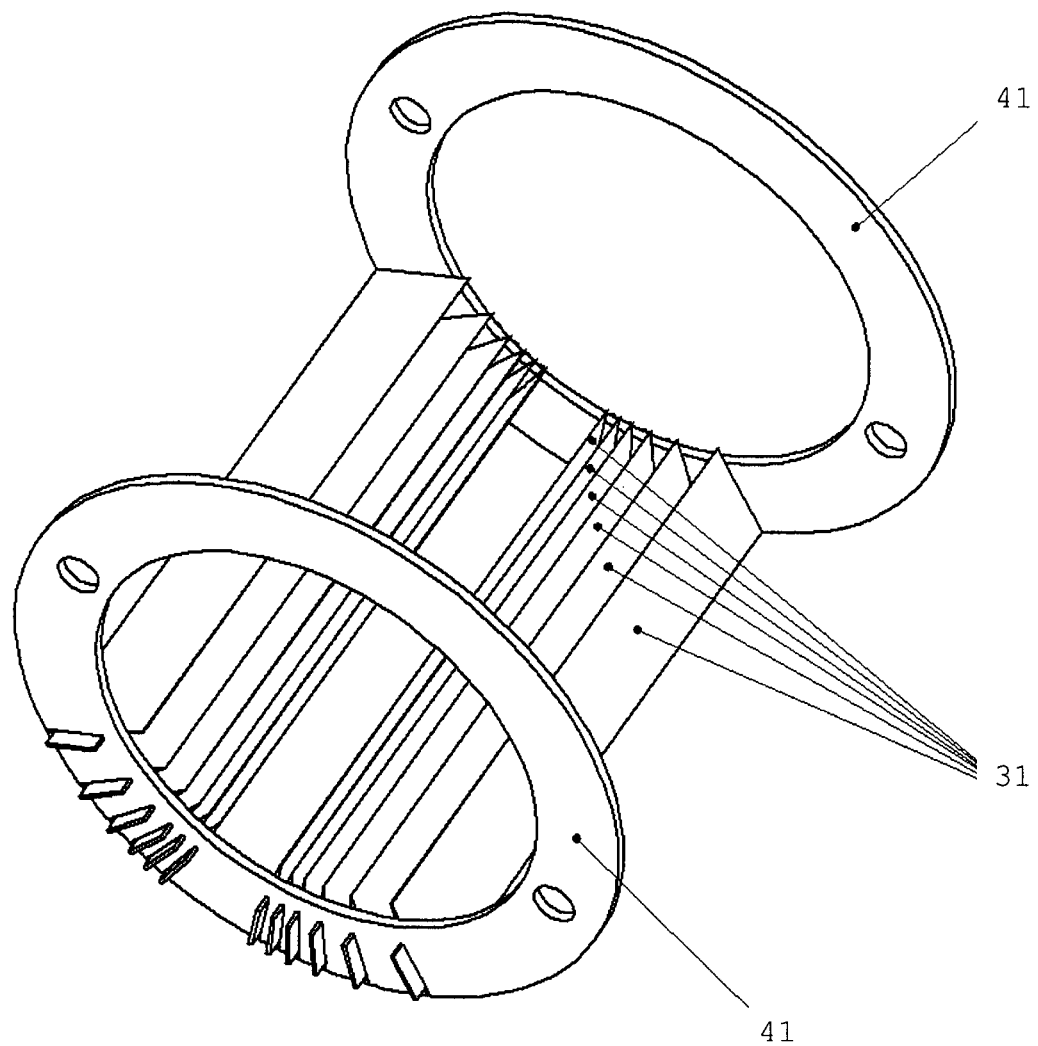
FIG. 4 depicts the fins of the optical imaging system shown in FIG. 2 in perspective view.

FIG. 4 shows a perspective view of the fins 31, 31' depicted in FIGS. 2 and 3 in cross-section. The fins 31, 31' extend along the rotation axis of the tube 29/the measurement chamber 21, the rotation axis running in the longitudinal direction of the tube 29/the measurement chamber 21. In case of a non-circular cross-section of the measurement chamber 21 (e.g. for a measurement chamber in form of a box), the fins 31, 31' preferably also extend along the longitudinal axis of the measurement chamber 21. Straight fins 31, 31' are preferably used. However, the fins 31, 31' may also be curved, in particular ring-like. If the measurement chamber has a cuboidal form the fins 31, 31' are preferably arranged on that inner wall of the cuboid that is opposite to the detection unit 24.

One or more support rings 41 are preferentially provided for support of each fin 31, 31' in the longitudinal direction. One support ring 41 may be arranged at the upper end and one support ring 41 may be arranged at the lower end of the tube 29/the measurement chamber 21, the upper end and lower end as seen by a viewer of the embodiments depicted in FIGS. 2 and 3. Each fin 31, 31' is connected at each of its ends to a support ring 41. In FIGS. 2 and 4 the outermost fins are also designated with reference numeral 31 for simplicity.

It is to be understood that while certain embodiments of the present invention have been illustrated and described herein, the present invention is not to be limited to the specific embodiments described and shown.

The invention claimed is:

1. Optical imaging system comprising an illumination unit (23), a detection unit (24) and a measurement chamber (21) for receiving a subject to be examined, wherein the illumination unit (23) is arranged such in relation to the measurement chamber (21) that it can illuminate a subject placed inside the measurement chamber (21), characterized in that the measurement chamber (21) is provided with several fins (31, 31') for preventing stray light from reaching the detection unit (24), the several fins (31, 31') being arranged in such a way that at least some of the fins (31, 31') are in the field of view of the detection unit (24) with the fins (31, 31') being orientated such that the surfaces (31.1, 31.1') of the fins (31, 31') that are subjected to illumination by stray light are not visible to the detection unit (24).

2. Optical imaging system according to claim 1, wherein the several fins (31, 31') are arranged at an inner wall of the measurement chamber (21).

3. Optical imaging system according to claim 2, wherein each outermost fin (31') is mounted at the inner wall of the measurement chamber (21) at the intersection of an outermost ray (33) with the inner wall of the measurement chamber (21), wherein each outermost ray (33) is defined as ray passing through an edge (43) of an entry (40) of the detection unit (24) and through an edge (44) of a projection of a light receiving region of a sensor (45) of the detection unit (24) onto the subject plane (34) inside the measurement chamber (21), with the edge (43) of the entry (40) of the detection unit (24) being on the opposite side of an optical axis (35) of the optical imaging system (20) from the edge (44) of the projection of the light receiving region.

4. Optical imaging system according to claim 3, wherein the entry (40) of the detection unit (24) is formed as entrance pupil.

5. Optical imaging system according to claim 4, wherein the inclination of each outermost fin (31') corresponds to or is steeper than the inclination of a ray (37) running from the intersection of the respective outermost ray (33) with the inner wall of the measurement chamber (21) to the point of intersection (36) of a light beam of the illumination unit (23) with a surface of the subject to be examined.

6. Optical imaging system according to claim 4, wherein as point of intersection (36) of the light beam with the surface of the subject a virtual point of intersection is chosen corresponding to the point of intersection (36) that is as far away as possible from the inner wall of the measurement chamber (21) where the illumination unit (23) is arranged.

7. Optical imaging system according to claim 6, wherein the virtual point of intersection (36) is situated further away from the illumination unit (23) as any real point of intersection of the light beam with the surface of a subject to be examined.

8. Optical imaging system according to claim 4, wherein fins (31) are arranged between each outermost fins (31') and the optical axis (35) at the inner wall of the measurement chamber (21), each fin (31) being mounted at the intersection of a respective ray (38) passing through an edge (43) of the entry (40) of the detection unit (24) and through the inwardly projecting end of an adjacent, more outwardly mounted fin (31, 31') on the opposite side of the optical axis (35).

9. Optical imaging system according to claim 8, wherein the inclination of each fin (31) that is arranged between an outermost fin (31') and the optical axis (35) corresponds to or is steeper than the inclination of a ray (39) running from the intersection of the respective ray (38) that runs through the edge (43) of the entry (40) of the detection unit (24) and through the inwardly projecting end of the adjacent, more outwardly mounted fin (31, 31') with the inner wall of the measurement chamber (21) to the point of intersection (36) of the light beam of the illumination unit (23) with the surface of the subject to be examined.

10. Optical imaging system according to claim 3, wherein the inclination of each outermost fin (31') corresponds to or is steeper than the inclination of a ray (37) running from the intersection of the respective outermost ray (33) with the inner wall of the measurement chamber (21) to the point of intersection (36) of a light beam of the illumination unit (23) with a surface of the subject to be examined.

11. Optical imaging system according to claim 3, wherein as point of intersection (36) of the light beam with the surface of the subject a virtual point of intersection is chosen corresponding to the point of intersection (36) that is as far away as possible from the inner wall of the measurement chamber (21) where the illumination unit (23) is arranged.

12. Optical imaging system according to claim 11, wherein the virtual point of intersection (36) is situated further away from the illumination unit (23) as any real point of intersection of the light beam with the surface of a subject to be examined.

13. Optical imaging system according to claim 11, wherein the distance between the rotation axis (30) of the measurement chamber (21) and the point of intersection (36) is between 0 mm and 20 mm, in particular 5 mm.

14. Optical imaging system according to claim 3, wherein fins (31) are arranged between each outermost fins (31') and the optical axis (35) at the inner wall of the measurement chamber (21), each fin (31) being mounted at the intersection of a respective ray (38) passing through an edge (43) of the entry (40) of the detection unit (24) and through the inwardly projecting end of an adjacent, more outwardly mounted fin (31, 31') on the opposite side of the optical axis (35).

15. Optical imaging system according to claim 14, wherein the inclination of each fin (31) that is arranged between an outermost fin (31') and the optical axis (35) corresponds to or is steeper than the inclination of a ray (39) running from the intersection of the respective ray (38) that runs through the edge (43) of the entry (40) of the detection unit (24) and through the inwardly projecting end of the adjacent, more outwardly mounted fin (31, 31') with the inner wall of the measurement chamber (21) to the point of intersection (36) of the light beam of the illumination unit (23) with the surface of the subject to be examined.

16. Optical imaging system according to claim 1, wherein the measurement chamber (21) has the shape of a hollow tube (29).

17. Optical imaging system according to claim 1, wherein the detection unit (24) is arranged on that side of the measurement chamber (21) that is opposite to the side of the measurement chamber (21) where the illumination unit (23) is arranged.

18. Optical imaging system according to claim 1, wherein the fins (31, 31') extend in the longitudinal direction of the measurement chamber (21).

19. Optical imaging system according to claim 18, wherein the fins (31, 31') are held by one or more support rings (41).

20. Optical imaging system according to claim 1, wherein the fins (31, 31') are ring-like.

* * * * *

UNITED STATES PATENT AND TRADEMARK OFFICE
CERTIFICATE OF CORRECTION

| | |
|---|---|
| PATENT NO. | : 9,255,882 B2 |
| APPLICATION NO. | : 14/122832 |
| DATED | : February 9, 2016 |
| INVENTOR(S) | : Kai Hassler et al. |

It is certified that error appears in the above-identified patent and that said Letters Patent is hereby corrected as shown below:

Title Page, item (87)

Please correct the PCT Publication Date, namely,
August 1, 2011

To read as follows:
August 11, 2011

Signed and Sealed this
Twenty-fourth Day of May, 2016

Michelle K. Lee
*Director of the United States Patent and Trademark Office*